United States Patent [19]

Huff et al.

[11] 4,381,302

[45] Apr. 26, 1983

[54] (6Aα,10Aα,11Aα)-2-(2-PYRIDINYL)-1,3,4,6,6A,7,8,9,10,10A,11,11A-DODECAHYDRO-2H-PYRAZINO]1,2-B]ISOQUINOLINE AND DERIVATIVES

[75] Inventors: Joel R. Huff, Gwynedd; Stella W. King; Walfred S. Saari, both of Lansdale, all of Pa.

[73] Assignee: Merck & Co., Inc., Rahway, N.J.

[21] Appl. No.: 267,325

[22] Filed: May 26, 1981

[51] Int. Cl.$^3$ .................. A61K 31/495; C07D 471/04
[52] U.S. Cl. ...................... 424/250; 544/344
[58] Field of Search .......................... 424/250; 544/344

[56] References Cited

U.S. PATENT DOCUMENTS

| | | | |
|---|---|---|---|
| 2,958,694 | 11/1960 | Jannsen | 260/268 |
| 3,773,951 | 11/1973 | Rodriguez | 424/250 |
| 4,078,063 | 3/1978 | Lumma et al. | 424/250 |
| 4,081,542 | 4/1978 | Lumma et al. | 425/250 |
| 4,082,844 | 4/1978 | Lumma et al. | 424/250 |

OTHER PUBLICATIONS

Thunus et al., *Ann. Pharm. Fran*, 32, 569–574, (1974).
Saxena et al., *Indian J. Chem.*, 13, 230–237, (1975).

*Primary Examiner*—Mark L. Berch
*Attorney, Agent, or Firm*—William H. Nicholson; Mario A. Monaco

[57] ABSTRACT

(6aα,10aα,11aα)-2-(2-pyridinyl)-1,3,4,6,6a,7,8,9,10,-10a,11,11a-dodecahydro-2H-pyrazino[1,2-b]isoquinoline and derivatives or acid addition salts thereof are selective $\alpha_2$-adrenergic receptor antagonists and thereby useful as antidepressant agents and for treating sedation caused by antihypertensive therapy.

9 Claims, No Drawings

(6Aα,10aα,11aα)-2-(2-PYRIDINYL)-1,3,4,6,6a,7,8,9,10,10a,11,11a-DODECAHYDRO-2H-PYRAZINO[1,2-b]ISOQUINOLINE AND DERIVATIVES

BACKGROUND OF THE INVENTION

This invention is concerned with novel (6aα,10aα,11aα)-2-(2-pyridinyl)-1,3,4,6,6a,7,8,9,10,10a,11,11a-dodecahydro-2H-pyrazino[1,2-b]isoquinoline and derivatives or pharmaceutically acceptable salts thereof which have antidepressant activity and the ability to counteract the sedative side effect of antihypertensive agents. It also relates to a process for preparing the novel compounds, pharmaceutical compositions comprising the novel compounds and to a method of treating depression or antihypertensive agent induced sedation with the novel compounds.

2-Piperazinyl-5 (and/or 6)-substituted pyridines (U.S. Pat. No. 4,078,063) are known anorexigenic agents which are also said to have antidepressant activity by virtue of their pharmacological influence on serotonin levels.

Now, with the present invention there is provided (6aα,10aα,11aα)-2-(2-pyridinyl)-1,3,4,6,6a,7,8,9,10,-10a,11,11a-dodecahydro-2H-pyrazino[1,2-b]isoquinoline and derivatives which are antidepressant agents and have the ability to counteract the sedative effect of antihypertensive agents by virtue of their ability to selectively antagonize $\alpha_2$-adrenergic receptor sites.

The concept that the complex clinical state of depression is linked to a functional deficiency of monoamines in the central nervous system is now widely accepted. Numerous biochemical and clinical observations support the proposal that many forms of depressive illness are associated with reductions in adrenergic activity at functionally important sites in the brain. Thus, classical antidepressive drugs, such as amitriptyline and imipramine, are believed to act by blocking the neuronal reuptake of norepinephrine and/or serotonin, thereby enhancing the availability of the monoamines as neurotransmitters.

In addition to $\alpha_1$-adrenergic receptors which mediate postsynaptic responses to the neurotransmitter norepinephrine, other adrenergic receptors are present at or near sympathetic terminals. These latter receptors, $\alpha_2$-adrenergic receptors, form part of a negative feedback system which modulates sympathetic neurotransmission by controlling the impulse-induced release of norepinephrine from presynaptic terminals. Activation of $\alpha_2$-adrenergic receptors results in a decrease in the amount of norepinephrine normally released from the nerve terminals by nerve impulses while antagonism of $\alpha_2$-adrenergic receptors increases norepinephrine release. Therefore, molecules that block $\alpha_2$-adrenergic receptors afford an alternate approach to enhancement of noradrenergic function and the treatment of depression associated with an absolute or relative deficiency of adrenergic function.

Mianserin, a clinically effective antidepressant which has been reported to have minimal in vivo norepinephrine reuptake inhibiting properties, blocks $\alpha_2$-adrenergic receptors. However, mianserin fails to exhibit any important selectivity for $\alpha_1$- or $\alpha_2$-adrenergic receptors suggesting that mianserin, in vivo, blocks $\alpha_1$-receptors at about the same dose required to block $\alpha_2$-receptors (Clineschmidt et al., *Arch. Int. Pharmacodyn. Ther.*, 242, 59 (1979)).

The compounds of the present invention, being highly selective for the $\alpha_2$-adrenergic receptor, have definite therapeutic advantages over the more non-selective $\alpha_1$-, $\alpha_2$-antagonists. Since $\alpha_1$- (or post-synaptic) blockade opposes the increase in nor-adrenergic transmission initiated through $\alpha_2$-blockade, compounds that selectively antagonize $\alpha_2$-adrenergic receptors promote enhanced neurotransmission at nor-adrenergic synapses. In addition, molecules with reduced $\alpha_1$-receptor blocking properties, such as the compounds of the present invention, produce less orthostatic hypotension, an undesirable side-effect (Synder, *Pharmakopsychiat*, 13, 62 (1980)).

Sedation, the limiting side effect produced by some antihypertensive agents, is believed to be associated with stimulation of presynaptic $\alpha_2$-adrenergic receptors. However, the lowering of blood pressure is not related to these receptors, but rather to postsynaptic adrenergic receptors (Birch et al., *Br. J. Pharmacol.*, 68, 107P (1979)). Selective $\alpha_2$-receptor antagonists should be useful in reducing the adverse effect of sedation produced by some antihypertensive drugs. Thus, the selective $\alpha_2$-receptor blocker, yohimbine, antagonizes the sedation produced by clonidine (Drew et al., *Br. J. Pharmacol.*, 67, 133 (1979)) and the locomotor depressant effects of methyldopa in rats (Clineschmidt et al., *Arch. Int. Pharmacodyn. Ther.*, 244, 231 (1980)). In addition, yohimbine has been reported to reduce clonidine-induced sedation in man (Autret et al., *Eur. J. Clin. Pharmacol.*, 12, 319 (1977)).

The compounds of the present invention, being highly selective for the $\alpha_2$-adrenergic receptor, effectively reduce the sedative effects of antihypertensive agents without affecting the blood pressure lowering properties.

DETAILED DESCRIPTION OF THE INVENTION

This invention is concerned with a compound of structural formula:

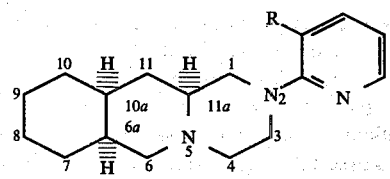

or a pharmaceutically acceptable salt thereof, wherein:
R is
(1) hydrogen;
(2) halo, such as chloro, bromo, iodo or fluoro, especially fluoro or bromo;
(3) $C_{1-4}$ alkyl, especially methyl;
(4) cyano;
(5) $C_{1-4}$ alkoxy, especially methoxy;
(6) trifluoromethyl; or
(7) nitro The pharmaceutically acceptable salts coming within the purview of this invention include the pharmaceutically acceptable acid-addition salts. Acids useful for preparing these acid-addition salts include, inter alia, inorganic acids, such as the hydrohalic acids (e.g., hydrochloric and hydrobromic acid), sulfuric acid, nitric acid, and phosphoric acid, and organic acids such as maleic, fumaric tartaric, citric, acetic, benzoic, 2-acetoxybenzoic, salicylic, succinic acid, theophylline, 8-chlorotheophylline, p-aminobenzoic, p-acetamidobenzoic, methanesulfonic, or ethane disulfonic.

The novel compounds of the present invention are prepared by reaction of 2-X-3-R-pyridines of formula II with (6a$\alpha$, 10a$\alpha$, 11a$\alpha$)-1,3,4,6,6a,7,8,9,10,10a, 11,11a-dodecahydro-2H-pyrazino[1,2-6]isoquinoline of formula I.

The reaction sequence is as follows:

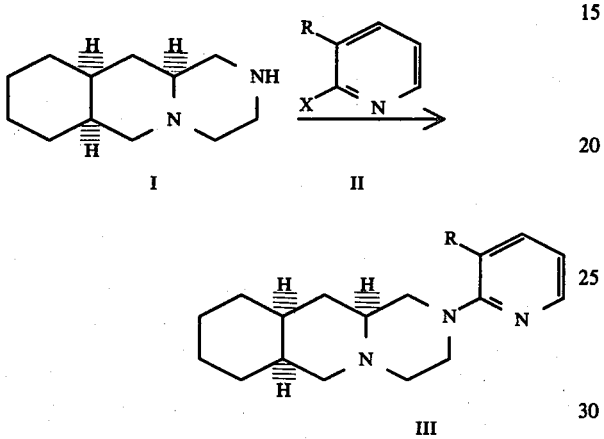

X is halogen, especially chloro or bromo, $C_{1-5}$alkylsulfonyloxy, such as methanesulfonyloxy; or arylsulfonyloxy such as, benzenesulfonyloxy or toluenesulfonyloxy.

The reaction takes place at temperatures ranging from about ambient to about 200° C., preferably under an inert atmosphere, e.g. $N_2$, He or Ar, until a substantial amount of desired compound of formula III is obtained, typically for a period of from about 0.25 to about 5 days, preferably from about 0.5 to about 3 days.

The reaction may be conducted neat, in the absence of solvent or in an inert organic solvent such as a $C_{2-5}$ alkanol, preferably butanol, or acetonitrile, dimethylformamide, or dimethylsulfoxide.

In the novel method of selectively antagonizing $\alpha_2$-adrenergic receptors in a patient a novel compound or pharmaceutically acceptable salt thereof, is administered in an amount ranging from about 0.01 to about 20 mg per kg of body weight per day, preferably from about 0.1 to about 10 mg per kg of body weight per day in a single dose or in 2 to 4 divided doses.

These doses are useful for treating depression or for treating sedation caused by antihypertensive chemotherapy.

The compounds, or pharmaceutically acceptable salts thereof, of the present invention, in the described dosages, are administered orally, intraperitoneally, subcutaneously, intramuscularly, or intravenously. They are preferably administered orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

EXAMPLE 1

(6a$\alpha$,10a$\alpha$,11a$\alpha$)-2-(2-pyridinyl)-1,3,4,6,6a,7,8,9,10,-10a,11,11a-dodecahydro-2H-pyrazino[1,2-b]isoquinoline dihydrochloride

Step A: Preparation of Methyl 1,2,3,4,4a,5,6,7,8,8a-Decahydroisoquinoline-3-carboxylate Methyl 1,2,3,4-tetrahydroisoquinoline-3-carboxylate hydrochloride (2.3 g, 10 mmol) in 200 ml absolute ethanol is hydrogenated at 50 psi, room temperature, using 0.6 g 5% Rh/C catalyst. After the theoretical amount of hydrogen is taken up (36 hours), the catalyst is filtered and the filtrate is evaporated to dryness. The residue is dissolved in methylene chloride and washed with a saturated solution of sodium carbonate. The organic phase is dried ($Na_2SO_4$) and acidified with ethanolic HCl. Evaporation of the solvent yields 2.0 g of the product as a diastereomeric mixture which is used without further separation.

Step B: Preparation of (6a$\alpha$,10a$\alpha$,11a$\alpha$)-1,3,4,6,6a,7,8,9,10,10a,11,11a-Dodecahydro-2H-pyrazino-[1,2-b]isoquinoline-1,3-dione A mixture of methyl 1,2,3,4,4a,5,6,7,8,8a-decahydroisoquinoline-3-carboxylate (5.0 g, 21.4 mmol), 2-bromoacetamide (2.95 g, 21.4 mmol), and potassium carbonate (7.1 g, 51.4 mmol) in 25 ml dimethylformamide is stirred at room temperature for 30 hours. The reaction is then diluted with water and extracted with ethyl acetate. The organic layer is separated, washed thoroughly with water, washed with brine, dried ($MgSO_4$), and concentrated. The residue is dissolved in 60 ml methanol and treated with sodium methoxide (1.39 g, 25 mmol). After stirring for 17 hours at room temperature, the solvent is evaporated. Water is added, and the pH is adjusted to 6.8-7, causing a solid to separate. This solid, which is a diastereomeric mixture is chromatographed over silica gel, eluting with 15% ethyl acetate/85% chloroform (v/v) to obtain 1.6 g of the desired product, m.p. 188°-189° C.

Step C: Preparation of (6a$\alpha$,10a$\alpha$,11a$\alpha$)-1,3,4,6,6a,7,8,9,10,10a,11,11a-Dodecahydro-2H-pyrazino-[1,2-b]isoquinoline Dihydrochloride Hydrate A solution of (6a$\alpha$,10a$\alpha$,11a$\alpha$)-1,3,4,6,6a,7,8,9,10,-10a,11,11a-Dodecahydro-2H-pyrazino-[1,2-b]isoquinoline-1,3-dione (1.6 g, 7.2 mmol) and bis(2-methoxyethoxy)aluminum hydride (50.8 mmol) in 120 ml of dry tetrahydrofuran is refluxed under nitrogen for 2 hours. After cooling the reaction, a saturated solution of sodium potassium tartrate is added cautiously. The organic layer is separated, dried ($Na_2SO_4$), and concentrated. The residue is taken up in ether and acidified with ethanolic HCl. The salt which separates is filtered and recrystallized by dissolving in a minimum of a 1:1 (by volume) mixture of ethanol and methanol and adding ether to incipient cloudiness to yield 1.5 g of product, m.p. 263°-266° C.

Step D: Preparation of (6aα,10aα,11aα)-2-(2-Pyridinyl)-1,3,4,6,6a,7,8,9,10,-10a,11,11a-Dodecahydro-2H-pyrazino[1,2-b]isoquinoline Dihydrochloride Hydrate A mixture of (6aα,10aα,11aα)-1,3,4,6,6a,7,8,9,10,-10a,11,11a-dodecahydro-2H-pyrazino[1,2-b]isoquinoline dihydrochloride hydrate (1.38 g, 4.8 mmol), 2-fluoropyridine (0.63 g, 6.5 mmol), and K₂CO₃ (2.34 g, 16.9 mmol) in 50 ml dimethylformamide is heated in an oil bath at 70° C. for 68 hours, then at 95° C. for 8 hours, and finally at 130° C. for 2 hours. After evaporating the dimethylformamide in vacuo, the residue is diluted with ethyl acetate and filtered. The filtrate is concentrated and chromatographed over silica gel, eluting with chloroform saturated with NH₃/hexane (3:1 by volume). The crude product is collected, dissolved in ethanol and acidified with ethanolic HCl. Recrystallization of the resulting salt from ethanol/ether affords 0.29 g of the desired product, m.p. 201°–210° C.

EXAMPLE 2

(6aα,10aα,11aα)-2-(3-Fluoro-2-pyridinyl)-1,3,4,6,6a,7,8,9,10,10a,11,11a-dodecahydro-2H-pyrazino[1,2-b]isoquinoline Dihydrochloride A mixture of (6aα,10aα,11aα)-1,3,4,-6,6a,7,8,9,10,-10a,11,11a-dodecahydro-2H-pyrazino[1,2-]isoquinoline dihydrochloride hydrate (1.38 g, 4.8 mmol), 2-chloro-3-fluoropyridine (0.85 g, 6.5 mmol), and potassium carbonate (2.34 g, 16.9 mmol) in 50 ml of dimethylformamide is heated at 130° C. for 4 hours. After evaporating the solvent in vacuo, the residue is diluted with ethyl acetate and filtered. The filtrate is concentrated and chromatographed over silica gel, eluting with chloroform saturated with NH₃/hexane (3:1 by volume). The crude product is collected, dissolved in ethanol, and acidified with ethanolic HCl. Recrystallization of the resulting salt from ethanol/ether affords the desired product.

Employing the procedure substantially as described in Example 2 but substituting for the 2-chloro-3-fluoropyridine used therein an equimolecular amount of the 2-chloro-3-R-pyridines wherein R is —Cl, Br, I, —CH₃, —C₂H₅, —C₄H₉, —CN, —NO₂, —OCH₃, —OC₃H₇, or —CF₃, there are produced the corresponding novel compounds of Structure III,

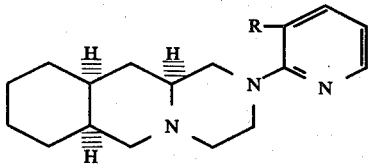

III wherein R is —Cl, —Br, —I, —CH₃, —C₂H₅, —C₄H₉, —CN, —NO₂, —OCH₃, —OC₃H₇ or —CF₃, respectively.

EXAMPLE 3

| Pharmaceutical Formulation | |
|---|---|
| Ingredient | Mg/capsule |
| (6aα, 10aα, 11aα)-2-(3-fluoro-2-pyridinyl)-1,3,4,6,6a,7,8,9,10,10a,11,11a-dodecahydro-2H-pyrazino-[1,2-b]-isoquinoline dihydrochloride | 6 |

| -continued | |
|---|---|
| Pharmaceutical Formulation | |
| Ingredient | Mg/capsule |
| starch | 87 |
| magnesium stearate | 7 |

The active ingredient, starch and magnesium stearate are blended together. The mixture is used to fill hard shell capsules of a suitable size at a fill weight of 100 mg per capsule.

What is claimed is:

1. A method of selectively antagonizing α₂-adrenergic receptors in a patient in need of such treatment which comprises the administration of an effective amount of a compound of structural formula:

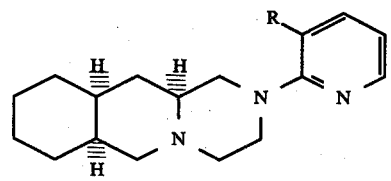

or a pharmaceutically acceptable salt thereof wherein R is
(1) hydrogen,
(2) halo,
(3) C₁₋₄alkyl,
(4) cyano,
(5) C₁₋₄alkoxy,
(6) trifluoromethyl, or
(7) nitro.

2. The method of claim 1 wherein R is hydrogen, fluoro, methyl, cyano, methoxy, trifluoromethyl or nitro.

3. The method of claim 2 wherein R is hydrogen or fluoro.

4. A compound of structural formula:

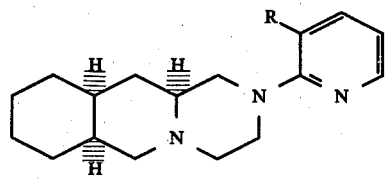

or a pharmaceutically acceptable salt thereof, wherein R is
(1) hydrogen,
(2) halo,
(3) C₁₋₄alkyl,
(4) cyano,
(5) C₁₋₄alkoxy,
(6) trifluoromethyl, or
(7) nitro.

5. The compound of claim 4, wherein R is hydrogen, fluoro, methyl, cyano, methoxy, trifluoromethyl or nitro.

6. The compound of claim 5, wherein R is hydrogen or fluoro.

7. A selective α₂-adrenergic receptor antagonist pharmaceutical composition consisting essentially of a pharmaceutically acceptable carrier and an effective $\alpha_2$-adrenergic receptor antagonist amount of a compound of structural formula:

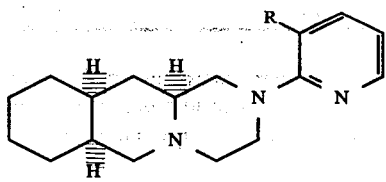

or a pharmaceutically acceptable salt thereof wherein R is
(1) hydrogen,
(2) halo,
(3) $C_{1-4}$alkyl,
(4) cyano,
(5) $C_{1-4}$alkoxy,
(6) trifluoromethyl, or
(7) nitro.

8. The pharmaceutical composition of claim 7 wherein R is hydrogen, fluoro, methyl, cyano, methoxy, trifluoromethyl or nitro.

9. The pharmaceutical composition of claim 8 wherein R is hydrogen or fluoro.